(12) United States Patent
Xu

(10) Patent No.: US 7,618,653 B2
(45) Date of Patent: Nov. 17, 2009

(54) BIOLOGICAL ARTIFICIAL NERVE GUIDE AND METHOD OF MAKING

(75) Inventor: Guo-Feng Xu, Guangzhou (CN)

(73) Assignee: Grandhope Biotech Co. Ltd., Guangzhou (CN)

( * ) Notice: Subject to any disclaimer, the term of this patent is extended or adjusted under 35 U.S.C. 154(b) by 0 days.

(21) Appl. No.: 11/641,187

(22) Filed: Dec. 18, 2006

(65) Prior Publication Data

US 2007/0141166 A1 Jun. 21, 2007

(30) Foreign Application Priority Data

Dec. 20, 2005 (CN) .................. 200510120792.7

(51) Int. Cl.
*A61K 35/12* (2006.01)
*A61K 9/16* (2006.01)
*A61K 38/00* (2006.01)
*A01N 37/18* (2006.01)

(52) U.S. Cl. ............... 424/520; 514/2; 524/56; 530/300

(58) Field of Classification Search ............ None
See application file for complete search history.

(56) References Cited

U.S. PATENT DOCUMENTS

| | | | | |
|---|---|---|---|---|
| 3,974,526 | A * | 8/1976 | Dardik et al. ............... | 623/1.41 |
| 4,920,203 | A * | 4/1990 | Tang et al. ................. | 525/409 |
| 5,080,670 | A | 1/1992 | Imamura et al. | |
| 5,217,492 | A | 6/1993 | Guire et al. | |
| 5,290,217 | A | 3/1994 | Campos | |
| 5,416,074 | A | 5/1995 | Rabaud et al. | |
| 5,447,536 | A | 9/1995 | Girardot et al. | |
| 5,549,666 | A | 8/1996 | Hata et al. | |
| 5,733,339 | A | 3/1998 | Girardot et al. | |
| 5,741,283 | A | 4/1998 | Fahy | |
| 5,758,420 | A | 6/1998 | Schmidt et al. | |
| 5,955,110 | A | 9/1999 | Patel et al. | |
| 6,008,292 | A | 12/1999 | Lee et al. | |
| 6,090,995 | A | 7/2000 | Reich et al. | |
| 6,106,555 | A * | 8/2000 | Yang ...................... | 623/11.11 |
| 6,117,979 | A | 9/2000 | Hendriks et al. | |
| 6,177,514 | B1 | 1/2001 | Pathak et al. | |
| 6,241,981 | B1 * | 6/2001 | Cobb et al. ................ | 424/93.1 |
| 6,251,117 | B1 | 6/2001 | Kringel et al. | |
| 6,458,889 | B1 | 10/2002 | Trollisas et al. | |
| 7,053,051 | B2 | 5/2006 | Hendriks et al. | |
| 7,060,103 | B2 | 6/2006 | Carr, Jr. et al. | |
| 7,077,851 | B2 | 7/2006 | Lutze et al. | |
| 2002/0042473 | A1 | 4/2002 | Trollisas et al. | |
| 2002/0081564 | A1 | 6/2002 | Levy et al. | |
| 2002/0091445 | A1 | 7/2002 | Sung et al. | |
| 2002/0099448 | A1 | 7/2002 | Hiles et al. | |
| 2002/0103542 | A1 | 8/2002 | Bilbo | |
| 2002/0138152 | A1 | 9/2002 | Francis et al. | |
| 2003/0013989 | A1 | 1/2003 | Obermiller et al. | |
| 2004/0202625 | A1 | 10/2004 | Daniloff et al. | |
| 2005/0136543 | A1 | 6/2005 | Torres et al. | |
| 2008/0195229 | A1 | 8/2008 | Quijano et al. | |

FOREIGN PATENT DOCUMENTS

WO WO 9822158 5/1998
WO WO 0032250 6/2000

OTHER PUBLICATIONS

Madison et al., Experimental Neurology, 88:767-772, 1985.*

* cited by examiner

*Primary Examiner*—Olga N. Chernyshev
*Assistant Examiner*—Stacey MacFarlane
(74) *Attorney, Agent, or Firm*—Raymond Sun

(57) ABSTRACT

A biological nerve guide for implantation into a human body is made by providing a natural animal tissue membrane, crosslinking and fixing the membrane, minimizing the antigens from the membrane, tanning the membrane, coupling an active layer to an inner surface of the membrane, cutting the membrane into a desired shape and size, positioning the cut membrane onto a rod-shaped mold so that the cut membrane assumes a cylindrical configuration, and attaching a spiral support to the outer surface of the cut membrane.

6 Claims, 3 Drawing Sheets

BIOLOGICAL ARTIFICIAL NERVE GUIDE AND METHOD OF MAKING

BACKGROUND OF THE INVENTION

1. Field of the Invention

The present invention relates to a medical prosthesis for human implantation, and in particular, to an artificial device for repairing neurons, such as a biological nerve guide.

2. Description of the Prior Art

Nerve tissues have regenerating power, and even the central nervous system has been discovered in recent years to possess regenerating power. However, nerve tissues are fragile and the regeneration speed is slow so that when neurons are damaged, natural regeneration and repair often are unable to reconnect the nerve because of the slow growth rate. Also, the repair path is often blocked by the faster growing surrounding regenerated tissues or scar tissue.

To address these problems, some scientists have tried to utilize a guide to connect the two ends of a defective nerve to prevent the path from being blocked, and this guide is called a nerve guide. Some conventional nerve guides are prepared from non-degradable materials so that irritation from foreign matter was always present while regeneration of nerve tissues was also adversely affected. Some of these conventional nerve guides are prepared from degradable materials such as polylactic acid or polyglycolic acid, but their degraded products exhibit localized acidity, adversely affecting the growth, the proliferation and the migration of nerve cells.

Other conventional nerve guides are produced from natural materials such as animal blood vessels, but conventional glutaraldehyde is utilized in the treatment process, resulting long-term residual toxicity and rather potent cellular toxicity while also adversely affecting the growth and proliferation of nerve cells. One of the serious drawbacks of the current nerve guides is the thick guide wall which does not allow the penetration of nutrients and the passage of blood supply, and the nerve cells inside the guide cannot obtain enough nutrients for desirable differentiation and migration to repair damaged tissue.

Another conventional nerve guide is produced from degradable natural materials such as animal collagen, but the mechanical properties such as flexibility, toughness, and kink resistance are not desirable. A noticeable drawback is that the degradation speed is difficult to match with the speed of nerve tissue regeneration, so that the treatment result is often uncertain.

SUMMARY OF THE DISCLOSURE

It is an object of the present invention to provide a biological nerve guide having good biocompatibility.

It is another object of the present invention to provide a biological nerve guide that can be penetrated by nutrients and allows for effective flow of blood supply while capable of being absorbed.

It is another object of the present invention to provide a method of preparing a biological nerve guide that meets the objects set forth above while overcoming the disadvantages described above.

In order to accomplish the objects of the present invention, the present invention provides a biological nerve guide for implantation into a human body, the nerve guide made by the following method:
 providing a natural animal tissue membrane;
 crosslinking and fixing the membrane;
 minimizing the antigens from the membrane;
 tanning the membrane;
 coupling an active layer to an inner surface of the membrane;
 cutting the membrane into a desired shape and size;
 positioning the cut membrane onto a rod-shaped mold so that the cut membrane assumes a cylindrical configuration having an outer surface; and
 attaching a spiral support to the outer surface of the cut membrane.

DETAILED DESCRIPTION OF THE PREFERRED EMBODIMENTS

Figure 1:
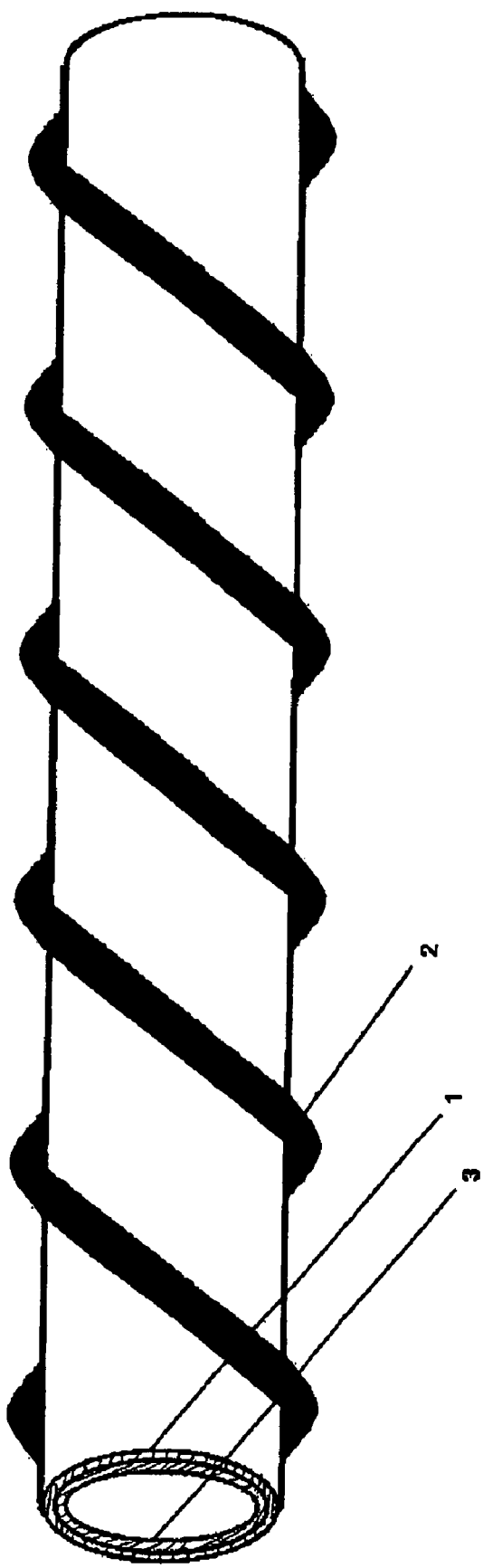
FIG. 1 is a perspective view of an artificial biological nerve guide according to one embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a biological nerve guide having a thin guide body prepared from animal membrane materials treated by crosslinked fixation with a non-aldehyde fixative, and having its antigens minimized with reagents having strong hydrogen bonding. A spiral support is formed by winding and immobilizing a long strip of the aforementioned membrane material around the guide wall.

Animal tissues are easily degraded or decomposed by microorganisms, so that crosslinking and fixation with a fixative is required. Conventionally, glutaraldehyde is utilized as a fixative, but glutaraldehyde produces toxic radicals. Aldehydes undergo crosslinking with proteins through the acetal reaction and toxic aldehydes are released when the crosslinked products are degraded, so that products fixed with an aldehyde have long-term residual toxicity. When non-aldehyde fixatives such as epoxides, diacyl diamides, diisocyanates, polyethylene glycol or carbodiimides are utilized as fixatives in place of aldehydes, this toxicity problem can be minimized or even eliminated. For example, when an epoxide is utilized to replace aldehyde-type fixatives, a ring-opening/crosslinking reaction occurs readily because epoxides are unstable, but the crosslinking product can be made very stable and not easily degraded by controlling the reaction condition. It is slowly degraded into polypeptides and amino acids and absorbed only when tissue growth and regeneration begin to devour it by secreting kallikrein, fibrinolysin and glucocorticoid hormone to help collagenase in the degradation. Such kind of passive degradation and tissue regeneration are occurring synchronously which is beneficial to tissue regenerative repair while having no residual toxicity of aldehydes. According to modern immunological theory, the antigenicity of animal tissues stems mainly from active groups located at specific sites and in specific conformations, and these active groups include —OH, —NH2, —SH, etc. The specific conformations result mainly from some specific hydrogen bonding formed by spiral protein chains. The specific sites and conformations are called antigen determinants. One or more active reagents (e.g., acid anhydrides, acyl chlorides, amides, epoxides, etc.) that react readily with these groups are utilized to bond with and block these groups when treating animal tissues so that the antigens can be effectively minimized or eliminated. Simultaneously, reagents with strong hydrogen bonding (e.g., guanidine compounds) are utilized to replace the hydrogen bonding that gives the specific configurations so that the configurations are altered and the antigenicity is effectively eliminated.

The wall of the nerve guide of the present invention is a thin permeable, semi-transparent membrane for insuring easy penetration of nutrients and microveins so that the need for regeneration of the nerve tissues is provided. A spiral support is provided on the guide wall to provide sufficient supporting power for the body of the guide, and to maintain a space for the path required for regeneration of nerve tissues. In addition, the winding, stretching and mechanical compatibility of the spiral support facilitate nerve repair at motor parts. Both the guide body and the spiral support are prepared using animal tissues as the starting materials, and the main component is collagen with a small quantity of glycoproteins, and they can be degraded to amino acids and polypeptides which can be absorbed by human bodies.

Tanning

The present invention uses an additional cross-linking method and a protein grafting method as a tanning process to improve the mechanical strength and toughness of the tissue. In this regard, a piece of animal membrane tissue usually provides poor mechanical properties (after harvesting). As used herein, "mechanical properties" means strength, toughness, rigidity and modulus. Both cross-linking and protein grafting can alter the mechanical properties of the tissue collagen (protein) matrix. Although cross-linking and protein grafting are common methods that are used to improve the mechanical properties of high polymers, it is still important to carefully determine the selection of reagents as well as the reaction conditions because protein can often be denatured. The length, density and distribution of cross-linkage are properly designed to ensure the stability of the tissue material and mechanical property.

For example, the molecular chain length of the crosslinking agent determines the cross-linking length. A longer chain results in better material flexibility. However, larger molecular chains are more difficult to penetrate into the collagen matrix. For example, when selecting an epoxy compound as the cross-linking agent, the molecular chain is preferably 4-8 hydrocarbons. The cross-linking density determines the cross-linking degree. Denser cross-linking results in better material stability, but denser cross-linking (especially when combined with a shorter molecular chain) can introduce a higher local stress in the material. A relatively uniform distribution of the cross-linking is ideal, but is usually difficult to obtain. Utilizing a lower concentration of the cross-linking solution, under a lower temperature, longer reaction duration, and repeating a few more times with the same reaction can often yield better results. As an example, when using an epoxy compound as the cross-linking agent as described in U.S. Pat. No. 6,106,555, good material stability, good flexibility, toughness and strength can be obtained by picking 4-8 hydrocarbon atom chain, with a concentration of 0.1 to 2%, under 4 to 24 degrees Celcius, reaction for 3-10 days, and repeating 2 to 5 times.

The chemical reagents can be the same as those described herein for use with tissue fixation. The protein grafting process can further improve the tissue's mechanical strength, toughness, rigidity and modulus. Protein grafting requires a large amount of polymer chains so that the nature of the protein structure can be changed substantially. Some high polymers can be grafted into collagen molecules by means of polycondensative primers. In order to avoid introducing hazardous subject matter into the human body, it is preferable to use biodegradable high polymers as the grafting agents, such as polyglycolic acid (PGA), polylactic acid (PLA) and others. These biodegradable polymers can be metabolized in the host environment through a tracarboxylic acid cycle just like for carbohydrates or fat metabolism. After such an extensive protein modification, up to 25 kGy gamma ray sterilization can be applied without adversely affecting the mechanical property of the tissue material. The total amount of protein grafting can be controlled optimally.

Active Layer

The surface of the nerve guide can also include an active layer. This active layer can contain a polypeptide or glycosaminoglycan. One example of the polypeptides is the polypeptide obtained from the condensation of 16 lysines (K16), glycine (G), arginine (R), asparagic acid (D), serine (S), proline (P) and cysteine (C), and said glycosaminoglycan is hyaluronic acid, chondroitin sulfate, dermatan sulfate, heparin, acetylheparin sulfate or keratan sulfate. These polypeptides or glycosaminoglycans exhibit a broad-spectrum adherence and enriching effect for growth factors or activate undifferentiated cells to perform oriented differentiation so that they are capable of exercising the function of inducing regenerative repair of organic tissues.

Materials

The body of the nerve guide, and the spiral support, can be made using animal intestinal membrane, pericardium, pleura or omentum.

Method

A method of preparing the biological nerve guide according to the present invention comprises the following steps:

1. Selection and cleaning of materials: Fresh animal membrane tissues are collected and sterilized with benzalkonium chloride or chlorhexidine, and trimmed to remove excessive impurities and irregular parts. The required membrane materials are obtained by taking and cleaning the neat and tough membrane materials.

2. Defatting: Fats and fat-soluble impurities in the membrane are extracted with an organic solvent.

3. Crosslinking fixation: The collagen molecules in the membrane are crosslinked and fixed with a non-aldehyde fixative.

4. Minimize antigens: The specific active group, namely —OH or —$NH_2$ or —SH, in the proteins of the membrane is blocked with an active reagent and the specific hydrogen bonding in the spiral chains of the proteins in the membrane is replaced by using a reagent having strong hydrogen bonding.

5. Tanning process: First, the preformed polymers are produced from monomers by synthesis. Second, the membrane is dehydrated with alcohol. Third, the preformed polymers are then grafted into collagen molecules by means of polycondensative primers. When using PGA as the grafting reagent, a small amount of glycolide may be used as the polycondensative primer. When using PLA as the grafting reagent, a small amount of lactide may be used as the polycondensative primer.

For example, using PLA as the protein grafting agent, the process could take 30-50 mg of lactide and dissolve it in 1000 ml of chloroform. 2-3 grams of triisobutyl aluminum can be added as the composite catalyst, and this solution can be stir-mixed for one to two hours under a temperature of 40-60 degrees Celcius. 100 ml of a 0.1 N NaOH solution is then added and stir-mixed for 30-60 minutes to destroy the catalyst. Then take away the separated water layer (with catalyst) and have the preformed polymers ready. Immerse the dehydrated membrane into the preformed polymer solution. Add 0.1 to 2 g of lactide and 0.5 to 5 g of proprionic anhydride as an initiation catalyst and then stir-mix for 2-4 hours under a temperature of 34 to 40 degrees Celcius. Take out the membrane and put it into chloroform to clean away the residual preformed polymers. After rinsing with saline, the membrane is then immersed into saline for 12 to 24 hours to recover the water content. The membrane is now ready for the next processing step.

6. Coupling of active layer: An active surface layer is coupled to the surface of the guide body using a coupling agent. The active surface layer has an active component such as a polypeptide or glycosaminoglycan. Specifically, the surface of the membrane material is coupled with a polypeptide or glycosaminoglycan capable of adhering to growth factors to form an active surface layer.

7. Preparation of the nerve guide: The membrane material is glued on a rod-shaped mold with medical gel to form a guide body. Separately, the same (or different) membrane material is cut to a specific width and then glued on the surface of the guide body by winding spirally at a given distance in multiple layers to form a spiral support having a particular supporting power. Next, the mold is removed to yield the final product.

Fixative

The fixative applied in step 3 of the above method can be a reagent that crosslinks easily with protein molecules and is one or two reagents selected from epoxides, diacyl diamides, diisocyanates, polyethylene glycol or carbodiimides. This fixative may be an epoxy compound that has a hydrocarbon backbone, that is water-soluble, and which does not contain an ether or ester linkage in its backbone. This fixative is described in U.S. Pat. No. 6,106,555, whose entire disclosure is incorporated by this reference as though set forth fully herein. Examples include an epoxide, a diamide, a diisocyanate, a polyethylene glycol, or a carbodiimide, in that the epoxide may be a monocyclic epoxide, or a bicyclic epoxide, or it may be a low poly(epoxide) (such as low poly(ethylene oxide), poly(propylene oxide) or a glycidyl ether). The epoxide may be a monocyclic epoxide

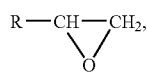

or a dicyclic epoxide

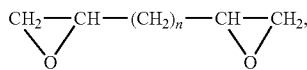

where R=H, $C_nH_{2n+1}$—, n=0-10, and may also be a lower polyepoxide such as polypropylene oxide.

Active Reagents

The active reagents in step 4 of the above method may be low molecular weight organic acid anhydrides, acyl chlorides, acyl amides, monocyclic oxides or epoxide, and the reagents having strong hydrogen bonding power are guanidine compounds.

Coupling Agent for Active Layer

The coupling agent utilized for coupling the polypeptide in step 6 of the above method may be a diacyl diamide, diacid anhydride, diepoxide or other bifunctional reagents capable of carrying out condensation with —$NH_2$, —OH and —COOH.

The present invention provides the following advantages. The final product is prepared by using natural biological materials such as animal tissues as the starting materials so that there is no immunogenicity, and minimal rejective reaction, while having excellent tissue compatibility and being capable of inducing division, proliferation and migration of nerve cells and promoting regeneration of nerve tissues. Pathway space required for the growth of nerve tissues is provided so that nutritional need for the growth of nerve tissues is supplied through penetration of nutrients and in-growth of blood vessels, thereby creating an excellent microenvironment for regenerative repair of the nerve tissues. After repair of the nerve tissues is completed, the biological nerve guide can be degraded and absorbed such that it is not present as a foreign matter.

EXAMPLE 1

Figure 2:
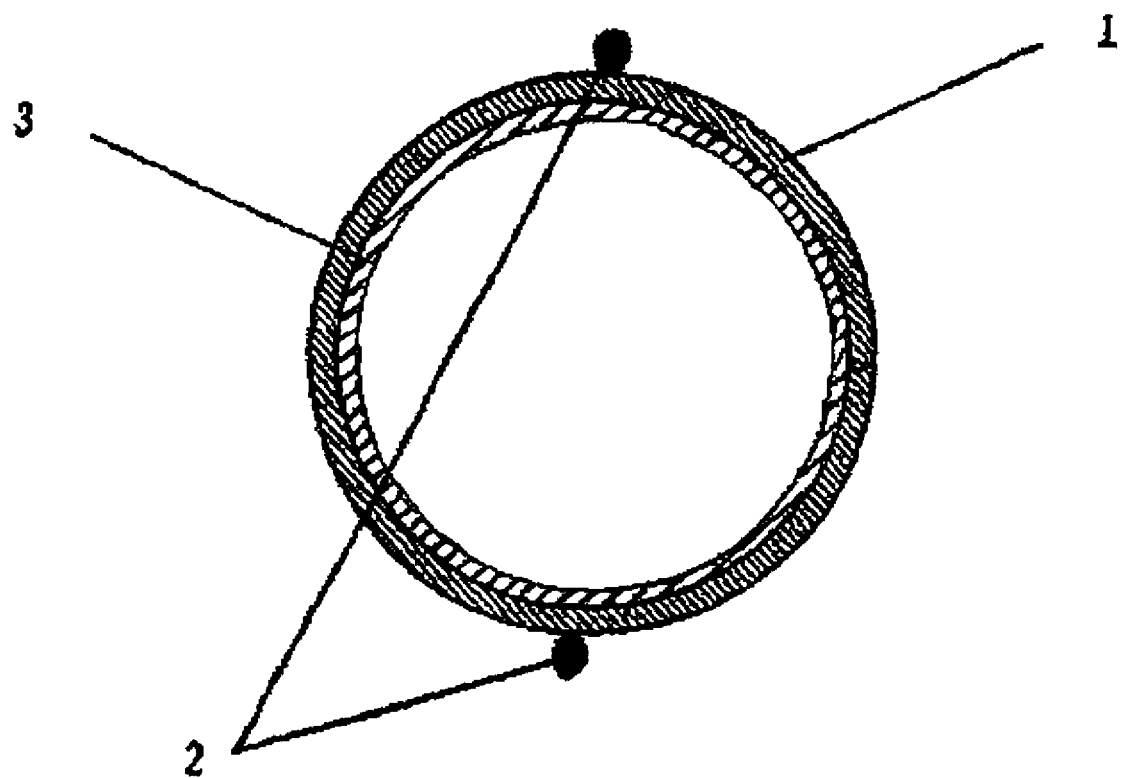
FIG. 2 is a cross-sectional view of the artificial biological nerve guide of FIG. 1.

Referring to FIGS. 1 and 2, fresh porcine membrane materials such as pericardium, omentum, pleura, diaphragm or small intestine membrane are excised, and the fatty materials and loose fibrous tissues are carefully removed, to trim the tough membrane to be as thin as possible. Then, the membrane is washed, cleaned and rinsed with water, and then the fats and fat-soluble impurities in the membrane materials are extracted using an organic solvent. The membrane will be used for the guide body 1 and the spiral support 2 shown in FIGS. 1-2.

Next, the solvent is removed and crosslinking fixation is conducted using a carbocyclic oxide.

After washing and freeze-drying, reaction with acetic anhydride or butyric anhydride is conducted to block the antigen groups, and the membrane is treated with Tris buffer solution of guanidine hydrochloride to alter the specific conformations of the antigens.

Polyglycolic acid prepolymer is then grafted on the collagen molecules to strengthen the durability using an acid anhydride as a condensation agent.

A diacid intramolecular anhydride is then utilized as a bifunctional coupling agent to couple the polypeptide obtained by condensing 16 lysines (K16), glycine (G), arginine (R), asparagic acid (D), serine (S), proline (P) and cysteine (C) or a glycosaminoglycan on the surface of the membrane material to form the active surface layer 3 on what would be the inner surface of the cylindrical guide body 1.

At this point, the membrane material is cut according to the desired specifications, and then glued on a rod-shaped mold to form the guide body 1 using medical gel. Separately the membrane material is cut into a long strip (e.g., about 0.5-2.0 mm wide) and rolled around and glued on the outer surface of the guide body 1 in a spiral manner to form the spiral support 2. Multiple layers of the spiral support 2 can be provided (by gluing) to increase the diameter of the nerve guide or to add another piece of spiral component until the required supporting power is attained. The nerve guide is then removed from the mold, washed, sterilized and then packaged by sealing with physiological saline solution being used as a preservative solution.

Figure 3A:
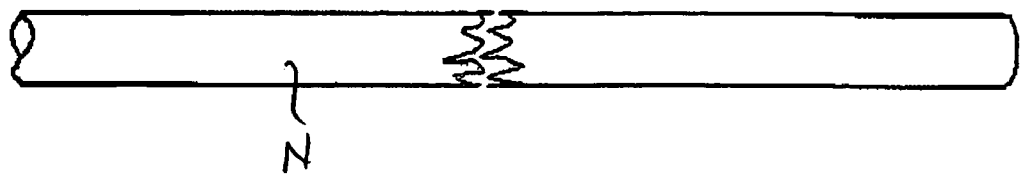
FIGS. 3A-3C illustrate the surgical repair of a damaged nerve using the nerve guide of FIG. 1.
Figure 3B:
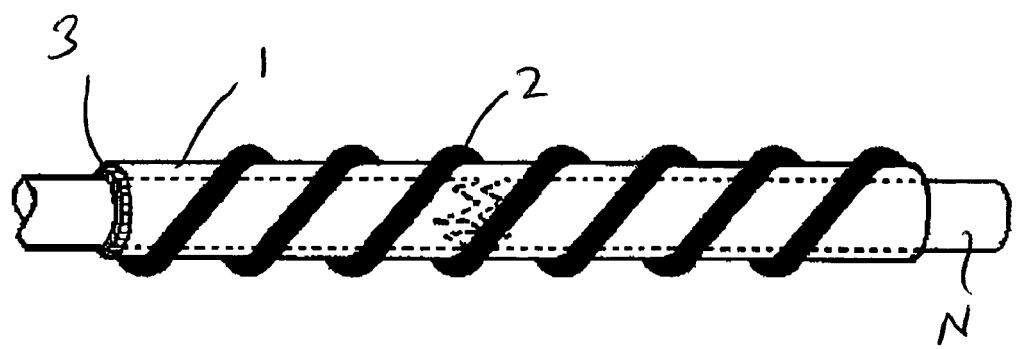
Figure 3C:
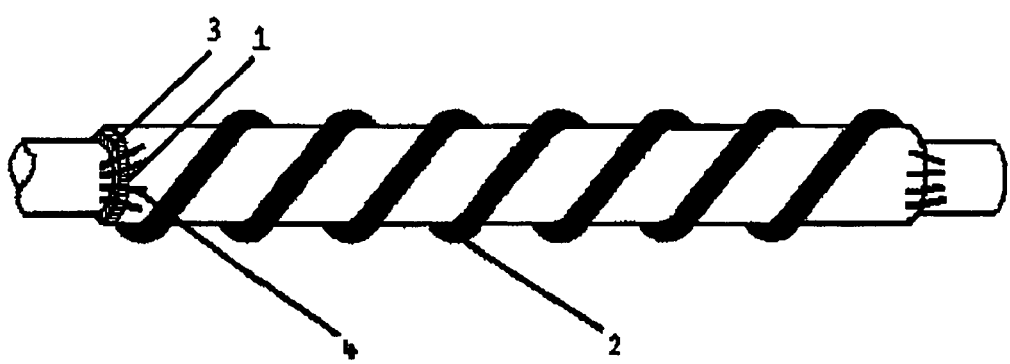

FIGS. 3A-3C illustrate how the nerve guide of FIGS. 1-2 can be used in the surgical repair of a damaged nerve N. FIG. 3A shows a nerve N that has been damaged (e.g., severed). As shown in FIG. 3B, the ends of the damaged nerve N can be inserted into the cylindrical bore of the nerve guide of FIG. 1, with the nerve guide serving as a connector. Sutures 4 can be applied to suture or attach the ends of the nerve guide to the damaged nerve.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method for preparing a biological nerve guide, comprising:
    providing a natural animal tissue membrane;
    crosslinking and fixing the membrane;
    applying an active reagent to block specific active groups in the proteins of the membrane;
    applying a guanidine compound to replace the specific hydrogen bonding in the spiral chains of the protein molecules in the membrane and alter its specific conformation;
    tanning the membrane;
    coupling a polypeptide or glycosaminoglycan to an inner surface of the membrane to form an active layer;
    cutting the membrane;
    positioning the cut membrane onto a rod-shaped mold so that the cut membrane assumes a cylindrical configuration having an outer surface; and
    attaching a spiral support to the outer surface of the cut membrane;
    wherein the polypeptide is the polypeptide obtained from the condensation of 16 lysines (K16), glycine (G), arginine (R), asparagic acid (D), serine (S), proline (P) and cysteine (C), and the glycosaminoglycan is hyaluronic acid, chondroitin sulfate, dermatan sulfate, heparin, acetylheparin sulfate or keratan sulfate.

2. The method of claim 1, wherein the cross-linking and fixing step is accomplished by applying an epoxy compound that has a hydrocarbon backbone, that is water-soluble, and which does not contain an ether or ester linkage in its backbone.

3. The method of claim 2, wherein the epoxy compound is an epoxide.

4. The method of claim 1, wherein the step of attaching a spiral support to the outer surface of the cut membrane includes the step of winding the spiral support in a non-overlapping manner.

5. A method for preparing a biological nerve guide, comprising:
    providing a natural animal tissue membrane;
    crosslinking and fixing the membrane;
    applying an active reagent to block specific active groups in the proteins of the membrane;
    applying a guanidine compound to replace the specific hydrogen bonding in the spiral chains of the protein molecules in the membrane and alter its specific conformation;
    tanning the membrane;
    coupling a polypeptide or glycosaminoglycan to an inner surface of the membrane to form an active layer;
    cutting the membrane;
    positioning the cut membrane onto a rod-shaped mold so that the cut membrane assumes a cylindrical configuration having an outer surface; and
    attaching a spiral support to the outer surface of the cut membrane;
    wherein the spiral support is cut from the same material as the membrane.

6. A method for preparing a biological nerve guide, comprising:
    providing a natural animal tissue membrane;
    crosslinking and fixing the membrane;
    applying an active reagent to block specific active groups in the proteins of the membrane;
    applying a guanidine compound to replace the specific hydrogen bonding in the spiral chains of the protein molecules in the membrane and alter its specific conformation;
    tanning the membrane;
    coupling a polypeptide or glycosaminoglycan to an inner surface of the membrane to form an active layer;
    cutting the membrane into a piece of material that is glued to a rod-shaped mold to form a tubular guide body;
    positioning the cut membrane onto a rod-shaped mold so that the cut membrane assumes a cylindrical configuration having an outer surface; and
    attaching a spiral support to the outer surface of the cut membrane.

* * * * *